United States Patent [19]

Kawasaki et al.

[11] Patent Number: 5,057,410
[45] Date of Patent: Oct. 15, 1991

[54] CHIMERIC MESSENGER RNA DETECTION METHODS

[75] Inventors: Ernest S. Kawasaki, Richmond; Francis P. McCormick, Albany; Owen O. Witto, Sherman Oaks, all of Calif.

[73] Assignee: Cetus Corporation, Emeryville, Calif.

[21] Appl. No.: 229,604

[22] Filed: Aug. 5, 1988

[51] Int. Cl.⁵ .................. C12Q 1/68; C07H 15/12; C12N 15/00
[52] U.S. Cl. .............................. 435/6; 536/27; 935/77; 935/78
[58] Field of Search ............... 435/6; 536/27; 935/77, 935/78

[56] References Cited

U.S. PATENT DOCUMENTS

| | | | |
|---|---|---|---|
| 4,681,840 | 7/1987 | Stephenson | 435/6 |
| 4,683,195 | 7/1987 | Mullis | 435/6 |
| 4,683,202 | 7/1987 | Mullis | 435/91 |

FOREIGN PATENT DOCUMENTS 0181635  5/1986  European Pat. Off.

OTHER PUBLICATIONS

Todd et al., Nature, V. 329 (10-15-87) pp. 599-604.
Harbarth et al., DNA, v. 4, n. 74 (1988) pp. 297-306.
Shtivelman et al., Cell, v. 47 (10-24-86) pp. 277-284.
Leder et al. (1983) Science 222:765-771.
Barletta et al. (1987) Science 235:1064-1067.
Preisler et al. (1987) Cancer Res. 47:847-880.
Pinto et al. (1987) Blood 70:1450-1457.
Heisterkamp et al. (1985) Nature 315:758-761.
Grosveld et al. (1986) Mol Cell 6(2):607-616.
Shtivelman et al. (1986) Cell 47:277-284.
Hermans et al. (1987) Cell 51:33-40.
Fainstein (1987) Nature 330:386-388.
Clark et al. (1988) Science 239:775-777.
Groffen et al. (1984) Cell 36:93-99.
Crescenzi et al. (1988) PNAS 85:4869-4873.
Lee et al. (1987) Science 237:175-178.
Powell et al. (1987) Cell 50:831-840.
Harbarth et al. (1988) DNA 7:297-306.
Todd et al. (1987) Nature 329:599-604.
Simpson et al. (1988) Biochem. Biophys. Res Comm. 151:487-492.
Lee et al. (1988) Science 239:1288-1291.
Byrne et al. (1988) Nucleic Acid Research 16:41.
Sarkar et al. (1988) Nucleic Acid Research 16:519.
Murakawa et al. (1988) DNA 7:287-295.
Lee et al. (1988) Blood 70:282a.
City of Hope (1988) Technology Licensing Opportunities p. 5.
Farr et al. (1988) PNAS 85:1629-1633.
Invitron (1988) The Digest 1:2.
Kawasaki et al. (1988) PNAS 85.

Primary Examiner—Robert A. Wax
Assistant Examiner—Mindy B. Fleisher
Attorney, Agent, or Firm—Stacey R. Sias; Richard M. Snead; Kevin R. Kaster

[57] ABSTRACT

The invention provides highly sensitive methods for detecting specific sequences contained in chimeric mRNA. The mRNA sequences are reverse transcribed into complementary DNA (cDNA), amplified by the Polymerase Chain Reaction, and detected by hybridization with a labeled sequence specific oligonucleotide probe. The method is particularly valuable for the detection of chimeric mRNAs experessed by activated oncogenes that result from aberrant genetic rearragements such as chromosomal translocations.

24 Claims, 3 Drawing Sheets

K562    1   2   3   4    HL-60

492-
369-

246-

123-

K562  Sup B15   1   2   3   4

492-
369-     
246-

123-

CHIMERIC MESSENGER RNA DETECTION METHODS

BACKGROUND OF THE INVENTION

1. Field of the Invention

The present invention relates to the field of molecular genetics and medical diagnosis. More specifically, the invention provides a method for detecting chimeric mRNA sequences containing a specific exon-exon junction by reverse transcription into complementary DNA (cDNA), amplification of the cDNA sequences by the Polymerase Chain Reaction (PCR), and analysis of the amplified material, if any. The method is especially useful for the detection as well as analysis of unique chimeric mRNA sequences indicative of normal or aberrant cell types, chimeric mRNA associated with certain stages of cellular development, and chimeric mRNA sequences associated with oncogenesis.

2. Description of the Related Art

This application describes methods of genetic analysis that utilize the polymerase chain reaction described in copending Ser. No. 063,647, filed June 17, 1987, which is a continuation-in-part of Ser. No. 899,513, filed Aug. 22, 1986, now abandoned, which is a continuation-in-part of Ser. No. 828,144, filed Feb. 7, 1986, which issued as U.S. Pat. No. 4,683,195, and which is a continuation-in-part of Ser. No. 791,308, filed Oct. 25, 1985, which issued as U.S. Pat. No. 4,683,202, and which is a continuation-in-part of now abandoned Ser. No. 716,975, filed Mar. 28, 1985. The polymerase chain reaction can employ a thermostable polymerase described in Ser. No. 143,441, filed Jan. 12, 1988, which is a continuation-in-part of copending Ser. No. 063,509, filed June 17, 1987, which issued as U.S. Pat. No. 4,889,818, which is a continuation-in-part of Ser. No. 899,241, filed Aug. 22, 1986, now abandoned. The polymerase chain reaction has been automated; an apparatus capable of carrying out the reaction is disclosed in related copending Ser. No. 899,061, filed Aug. 22, 1986, which is a continuation-in-part of Ser. No. 833,368, filed Feb. 25, 1986, now abandoned. The present invention also provides methods of dot-blot hybridization and so is related to copending Ser. No. 197,000, filed May 20, 1988, which is a continuation-in-part of Ser. No. 899,344, filed Aug. 22, 1986, now abandoned, which is a continuation-in-part of Ser. No. 839,331, filed Mar. 13, 1986, which is now abandoned. In addition, the invention discloses methods for using enzyme labeled oligonucleotide probes and so is related to Ser. No. 103,978, now abandoned in favor of continuation Ser. No. 437,311, filed Oct. 2, 1987, and is related to Ser. No. 104,200, filed Oct. 2, 1987, which has issued as U.S. Pat. No. 4,914,210. The disclosure of these related applications and patents are incorporated herein by reference.

The techniques of molecular biology have yielded new insight about disease processes at the molecular level. Gene cloning has made it possible to understand genetic fine structure and the mechanisms of gene regulation. As a result, the aberrant effects of genetic alteration, i.e. mutation, deletion, insertion, substitution or amplification are becoming better characterized. In turn, the techniques of molecular biology have moved from basic research to applied medicine with the development of new diagnostic tools for improved prognosis and treatment.

The detection of mRNA expressed from a particular gene is one approach in determining a gene's activity. The detection of mRNA is done primarily through the use of labeled hybridization probes. See, for example, Maniatis, T., et al. Molecular Cloning, A Laboratory Manual, Cold Spring Harbor Laboratory (1982). The hybridization can be done in solution or the RNA can be immobilized onto a membrane and subsequently detected as in the Northern format and RNA dot blot hybridizations. Traditional detection methods are limited by requiring large amounts of mRNA. If the mRNA of interest is present in low copy number, large amounts of biological material will need to be extracted and the mRNA enriched by such methods as density gradient centrifugation and oligo (dT)-cellulose chromatography. In addition, detection of mRNA sequences can be achieved by reverse transcription of the mRNA into cDNA and detection of the cDNA directly with a labeled hybridization probe. The cDNA can also be cloned into a plasmid and detected by colony hybridization. For diagnostic purposes, however, such methods for detecting mRNA sequences are impractical due to the cost of time, labor, and materials.

In recent years, the correlation of gene activity with disease state has focused on the association between proto-oncogene expression and the events of carcinogenesis. For example, Slamon, D. J., et al. Science 224: 256–262 (1984), demonstrated the expression of 15 proto-oncogenes by Northern analysis of RNA from fresh human tumors from 54 patients, representing 20 different tumor types. The study required the extraction of large tissue samples to obtain the 5 μg of RNA needed for the analysis.

Similar studies of proto-oncogene expression have shown the association between overexpression of a variety of genes and cancers, including: the neu/HER-2 mRNA and breast cancer, Van De Vijver, M. et al., Mol. Cell. Biol. 7: 2019–2023 (1987); c-MYC mRNA and breast cancer, Escot, C., et al. PNAS 83: 4834–4838 (1986); c-MYC mRNA in fresh tumor material from patients with hematopoietic malignancies, Rothberg, P. G. Mol. Cell. Biol. 4: 1096–1103 (1984); H-ras mRNA and breast cancer, Theillet, C., et al. Cancer Res. 46: 4776–4781 (1986); N-myc mRNA and neuroblastoma, Michitsch, R. W., et al. Mol. Cell. Biol. 4: 2370–2380, (1984); c-MYC mRNA and cervical cancer, Riou, G., et al. Lancet 1: 761–763 (1987); and c-, N-, or L-MYC mRNA and small cell lung cancer (SCLC) cell lines, Nau, M. M., et al. Nature 318: 69–73 (1985). In each case, large sample specimens had to be extracted to obtain sufficient amounts of mRNA for the analyses. Such analyses would be impossible with small samples taken for early diagnosis when tumor mass is barely discernable.

Genetic rearrangements such as chromosome translocation can also result in the expression of proto-oncogene mRNA. For example, Philadelphia chromosome (Ph[1], t[9;22] [q34; q11]) associated with chronic myeloid leukemia (CML) is a translocation that results in the combining of sites near or within the proto-oncogene c-ABL with a region of chromosome 22 called the breakpoint cluster region gene (BCR). The BCR-ABL sequence has been shown by Shtivelman, E. et al. Cell 47: 277–284 (1986) to express an 8.7 kb mRNA. The RNA analysis methods used, e.g., Northern blotting, S-1 mapping and RNAase protection, required large amounts of RNA and several days to complete. Such methods are impractical as diagnostic tools. U.S. Pat. No. 4,681,840 issued July 21, 1987, discloses single-stranded DNA probes for detecting BCR sequences and associated chromosome translocations.

In a similar manner, Northern blotting and S-1 mapping were used by Leder, P., et al. Science 222: 765-771 (1983), to show the disregulation of c-MYC expression from chromosome 8q24 in Burkitt's lymphoma. The rearrangement combines the c-MYC gene with one of three immunoglobulin loci on chromosomes 14(q32), 2(q13) or 22(q11), as described by Liein, G., Cell 32: 311 (1983).

RNA expression levels of the proto-oncogenes c-MYC, c-FOS, and c-FMS, were measured in bone marrow cells obtained from patients with acute myeloid leukemia (AML), Preisler, H. D., et al. Cancer Res. 47: 847-880 (1987). The results suggested the possible use of proto-oncogene expression patterns as a means of more accurately categorizing leukemic cell subtypes. The elevated expression of proto-oncogene mRNA has in some instances been found to be associated with chromosome deletion. For example, Barletta, C., et al. Science 235: 1064-1067 (1987), show that amplification and overexpression of the c-MYC locus accompanies deletion of the long arm of chromosome 6 and suggest an involvement in the pathogenesis of leukemias and lymphomas.

PCR amplification followed by oligonucleotide dot blot analysis was used to study RAS gene mutations in acute myeloid leukemia (AML). The study screened for point mutations in codons 12, 13, and 61 and found 27% of the patients contained mutations which were predominantly in codon 12, Farr, C. J., et al. PNAS 85: 1629-1633.

The use of RNA dot-blot hybridization is a common method to measure gene expression. Pinto, A., et al. Blood 70: 1450-1457 (1987), applied RNA dot-blot techniques to measure c-FOS oncogene expression in human hematopoietic malignancies. The method required isolation of the leukemic cells before RNA extraction, and large quantities of RNA were required for detection and quantitation of proto-oncogene expression.

Hybridization to DNA sequences is the primary approach for detecting altered gene structure. DNA hybridization lacks the sensitivity needed to discriminate diseased from healthy cells in the early stages of illness, e.g., for cancer diagnosis. Yoffe, G., et al. Blood 69: 961 (1987), showed 5% of a patient's lymphocytes must be leukemic before deletions and translocations in genomic DNA can be detected by Southern transfer. Although hybridization with DNA sequences allows detection of genomic fine structure and chromosomal rearrangement, the method indicates nothing about gene activity.

U.S. Pat. No. 4,683,202, incorporated herein by reference, discloses a method for amplifying specific nucleic acid sequences, called the Polymerase Chain Reaction (PCR). U.S. Pat. No. 4,683,195, incorporated herein by reference, discloses a method of using PCR for amplifying, detecting and cloning nucleic acid sequences. PCR causes the exponential amplification of target nucleic acid sequences from small amounts of material. The PCR process utilizes temperature regulated cycling of oligonucleotide primer hybridization and DNA polymerase mediated synthesis of target sequences from the hybridized primers. Because thermal denaturation of polymerase results in decreased amplification, the PCR format has been greatly simplified through the use of the thermostable DNA polymerase (Taq) isolated from the thermophilic bacterium, *Thermus aquaticus*. A process for amplifying, detecting, and cloning nucleic acid sequences using a thermostable enzyme is disclosed in U.S. application Ser. No. 063,647, filed June 17, 1987, incorporated herein by reference.

The isolation, cloning and physical properties of the Taq enzyme, together with stable enzyme compositions having a purified, thermostable polymerase enzyme such as Taq in a buffer containing one or more nonionic detergents are disclosed in U.S. application Ser. No. 063,509, filed June 17, 1987, incorporated herein by reference. The PCR amplification of translocated DNA sequences requires knowledge of the translocation junction. This is difficult when the translocation occurs randomly within long segments of DNA. For example, Groffen, J., et. al. Cell 36: 93-99 (1984), incorporated herein by reference, found that in 17 of 17 Ph[1] positive CML patients, the BCR breakpoint occurred within 5.8 kb, while the c-ABL breakpoint was dispersed along 100 kb.

The PCR amplification and analysis of mRNA via cDNA with a thermostable enzyme has been shown in commonly owned and copending U.S. patent application Ser. No. 899,513, filed Aug. 22, 1986. Powell, L. M., et al. Cell 50: 831-840 (1987), have applied PCR amplification of cDNA to the study of a novel form of tissue-specific RNA processing for apolipoprotein-B48 in the intestine. In addition, PCR amplification of double stranded cDNA has been used by Todd, J. A., et al. Nature 329: 599-604, to facilitate the cloning of the gene for HLA-DQ$\beta$.

SUMMARY

The present invention overcomes the complex, laborious, and uneconomical methods currently practiced in the art for the detection of specific mRNA sequences for diagnostic purposes. The methods of the invention are not only easier than what is currently known but also are many fold more sensitive. The methods can be used to detect chimeric mRNA expressed by a single oncogene of a neoplastic hemopoietic cell present in a sample of blood from a patient with the earliest stages of leukemia.

The invention provides methods for detecting the presence or absence of a chimeric mRNA in a biological sample, wherein the chimeric mRNA contains an exon-junction between a first and second exon, wherein said first exon is located nearer the 5' end of said chimeric mRNA than said second exon, said method comprising:

(a) synthesizing cDNA from RNA in said sample;

(b) contacting said cDNA with a first and second primer, wherein said first primer is homologous to a sequence contained in said first exon and said second primer is complementary to a sequence in said second exon;

(c) treating the mixture prepared in step (b) under conditions and with reagents suitable for carrying out the Polymerase Chain Reaction for the amplification of a cDNA sequence annealed with and located between said primers; and (d) determining if amplification has occurred.

Another aspect of the invention concerns oligonucleotide primers and probes for amplifying and detecting cDNA of specific chimeric mRNA sequences associated with chronic myeloid leukemia (CML), acute lymphocytic leukemia (ALL), and acute myeloid leukemia (AML).

A further aspect of the invention are kits for amplifying and detecting specific sequences of chimeric mRNA.

DESCRIPTION OF THE PREFERRED EMBODIMENTS

Definitions

Figure 1:
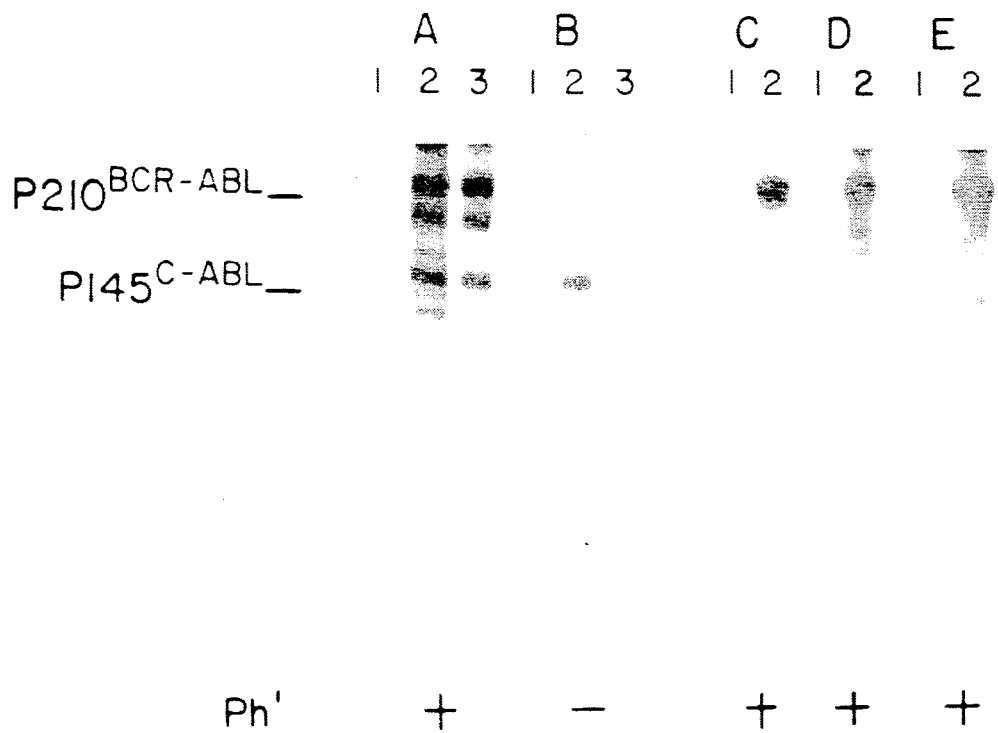
FIG. 1 depicts an autoradiograph that shows the immonoprecipitation and in vitro kinase activity of samples from 3 patients with CML. The karyotype of each sample is also indicated by the presence (+) or absence (−) of the Philadelphia chromosome (Ph[1]). A fourth patient specimen could not be analyzed because of the poor quality of the cells.

The following terms, as used herein, are defined as follows. The term "oligonucleotide" refers to primers, probes, oligomer fragments to be detected, oligomer controls and unlabeled blocking oligomers and is defined as a molecule comprised of two or more deoxyribonucleotide or ribonucleotides, preferably more than three. The exact size depends upon many factors, which in turn depend on the ultimate function or use of the oligonucleotide.

The term "primer" refers to an oligonucleotide, whether derived from a natural source, as in a purified restriction digest, or produced synthetically, which is capable of acting as a point of initiation of synthesis when placed under conditions in which synthesis of a primer extension product which is complementary to a nucleic acid strand is induced, i.e., in the presence of four different nucleoside 5′-triphosphates and an agent for polymerization, for example DNA polymerase or reverse transcriptase, in an appropriate buffer ("buffer" includes pH, ionic strength, cofactors, etc.) and at a suitable temperature.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the polymerization agent. The exact length of a primer depends on many factors, including temperature and source of primer and use in the method. For example, depending on the complexity of the target sequence, the oligonucleotide primer typically contains 15–25 nucleotides, although it may contain more or fewer nucleotides. Short primer molecules generally require cooler temperatures to form sufficiently stable hybrid complexes with the template.

The primers used herein are selected to be "substantially" complementary to the different strands of each specific sequence to be amplified. Therefore, the primers need not reflect the exact sequence of the template, but must be sufficiently complementary to hybridize with sequences of the amplified target. For example, a non-complementary nucleotide fragment may be attached to the 5′-end of the primer, with the remainder of the primer sequence being complementary to sequences of the amplified target. Alternatively, non-complementary bases or longer sequences can be interspersed into the primer, provided that the primer has sufficient complementarity with the sequence of the amplified target to hybridize therewith and thereby form a template for synthesis of the extension product of the other primer. In a preferred mode, the non-complementary nucleotide sequence encodes a restriction enzyme site.

"Chimeric mRNA" refers to mRNA sequences that contain at least two different exons that are spliced together to form an exon-exon junction. Preferably, these exons are from at least two different genes that are not spliced together under conditions required for normal growth, reproduction and function.

As used herein, the term "thermostable enzyme" refers to an enzyme which is relatively heat stable and which catalyzes the polymerization of nucleotides to form the primer extension products which are complementary to the nucleic acid strands of the amplified cDNA target sequence. Generally, the enzyme will initiate synthesis at the 3′-end of the target sequence utilizing the primer, and will proceed in the 3′-direction along the template until synthesis terminates. A purified thermostable enzyme and method for using it are described more fully in copending U.S. patent application Ser. No. 63,647, filed June 17, 1987, incorporated herein by reference.

General Modes

In general, the method for detecting specific chimeric mRNA sequences comprises extracting the RNA, copying the RNA into cDNA, amplifying a specific sequence contained in the cDNA that corresponds with sequences of the chimeric mRNA, and detecting the presence or absence of the amplified sequence.

The method is applicable to detecting any type of RNA, i.e., ribosomal, transfer, messenger and small nuclear RNAs. The extraction of different RNAs is commonly practiced by a variety of methods, as exemplified by the protocols in Maniatis, supra. The source of RNA can be from any type of organism, including plant, bacteria and animal.

The method is most preferred for the detection of chimeric mRNAs that contain exon-exon junctions. The method can be use to indirectly analyze the activity of a particular gene by detecting the chimeric mRNA which the gene expresses. As a result, not only can the method detect the activity of an aberrant gene that gives rise to chimeric mRNA which contain exons from normally unrelated genes (i.e., BCR/ABL), the method can also be used to detect abnormal activity of a normal gene (i.e., by detecting chimeric mRNA expressed at abnormal times or in abnormal amounts during cellular development).

The initiation of cDNA synthesis from mRNA is commonly done using oligo d(T) that is complementary with poly A containing mRNA or through the use of an oligonucleotide primer, herein called the "downstream primer", that is substantially complementary for sequences within the RNA molecule. The decision as to which type of oligonucleotide primer to use for initiating cDNA synthesis depends on the chimeric mRNA. Synthesis of cDNA from chimeric mRNA that contains a poly A tail can be initiated with oligo d(T). If the region to be amplified is located far away from the poly A tail, however (e.g., the chimeric mRNA produced from the BCR-ABL gene is approximately 8,500 bp long, so a particular region to be amplified could be several kb from the poly A tail), cDNA synthesis is most efficient when initiated with a downstream primer. The downstream primer is designed to hybridize with chimeric mRNA sequences that are on the 5' side of the poly A tail, preferably within the protein coding sequences and, most preferably, near the exon-exon junction. In addition, the downstream primer is used where the poly A sequence is absent, as is the case for ribosomal, transfer, small nuclear, and some messenger RNAs, e.g., histone messenger RNA. The synthesis of cDNA is most commonly achieved using reverse transcriptase (commercially available from such vendors as Bethesda Research Laboratories, Inc., P.O. Box 6009, Gaithersburg, Md. 20877, or Boehringer Manheim Biochemicals, 9115 Hague Road, P.O. Box 50816, Indianapolis, Ind. 46250) extracted from avian myeloblastosis virus (AMV) or murine leukemia virus (MuL V). Methods for synthesizing cDNA are described in Maniatis, supra., incorporated herein by reference.

The Polymerase Chain Reaction has been shown to be highly sensitive, capable of detecting the equivalent of a single gene from a single cell. Because of this great sensitivity, together with the facts that most RNAs are transcribed as many copies per cell and that there are many cells in a typical sample, a large percent of the chimeric mRNA of a sample can be degraded and still be detectable by the methods of the invention. This is of particular importance for the analysis of forensic samples.

The process for amplifying nucleic acid, called the "Polymerase Chain Reaction" method, is disclosed by Mullis in U.S. Pat. No. 4,683,202, incorporated herein by reference. The application of PCR for the detection and cloning of nucleic acid sequences using a thermostable enzyme is disclosed by Erlich et al. in U.S. application Ser. No. 063,467, filed July 17, 1987, incorporated herein by reference. In general, the amplification process involves an enzymatic chain reaction for preparing, in exponential quantities relative to the number of reaction steps involved, a specific nucleic acid sequence, given that the ends of the required sequence are known in sufficient detail so that oligonucleotide primers can be synthesized which will substantially hybridize to them and that a free 3' hydroxyl group of an oligonucleotide primer is available to initiate the chain reaction.

The chimeric mRNA will contain at least a first and second exon spliced together to form an exon-exon junction. The chimeric mRNA has a capped 5' (5' end), a second end with a free 3' hydroxyl (3' end), and the exon-exon junction in between. Thus, the first exon of the chimeric mRNA is closer to the 5' end than the second exon, which is closer to the 3' end than the first exon. The chimeric mRNA is transcribed into complementary DNA (cDNA) using reverse transcriptase in a manner well known in the art. During reverse transcription, the reverse transcriptase reads the chimeric mRNA sequences from the 3' end to the 5' end; synthesis of the cDNA initiates at the free 3' hydroxyl of an oligonucleotide primer that is annealed with the chimeric mRNA. Synthesis initiates from the 3' end of the primer, and proceeds toward the 5' end of the chimeric mRNA. The result is a cDNA copy of the chimeric mRNA. This cDNA has sequences complementary to the first exon located toward the 3' end and sequences complementary to the second exon located toward the 5' end. The cDNA also contains sequences complementary to sequences in the mRNA that span the exon-exon junction.

The cDNA copy of the chimeric mRNA is detected by first PCR amplifying sequences surrounding and containing the exon-exon junction and then hybridizing the amplified product with a sequence specific probe. To achieve amplification, two oligonucleotide primers are designed, the first being complementary with sequences of cDNA that are on the 3' side of the exon-exon junction contained in the cDNA and the second being homologous with sequences of cDNA that are on the 5' side of the exon-exon junction contained in the cDNA. When annealed, the free 3' hydroxyl of the first oligonucleotide primer allows initiation of a first DNA extension product that is complementary with sequences of cDNA. The first DNA extension product contains the exon-exon junction and sequences that are complementary to the second primer. Accordingly, the first DNA extension product will anneal with the second primer, and act as a template for the synthesis of a second DNA extension product that is homologous with sequences of the initial cDNA template. With repeated cycles of primer annealing, extension product synthesis, and primer melting, the product exponentially increases. The product is a discrete nucleic acid duplex that contains the exon-exon junction between two termini corresponding to the ends of the specific primers employed.

This amplified product is readily detectable by any number of ways known in the art. The product can be analyzed by gel electrophoresis and staining with ethidium bromide or the gel electrophoresed material can be transferred to a membrane and hybridized with an oligonucleotide probe as described by Southern, E. J. Mol. Biol. 98: 503 (1975), incorporated herein by reference. The amplified product can be applied directly on a membrane and detected by dot blot hybridization as described U.S. patent application Ser. Nos. 839,331 and 899,344, incorporated herein by reference. The amplified product can be labeled by using labeled oligonucleotide primers during the Polymerase Chain Reaction. This labeled product can be hybridized with a probe immobilized on a solid support as described in commonly owned and copending U.S. patent application Ser. No. 197,000, filed May 20, 1988, incorporated herein by reference.

The probe can be substantially complementary with any sequence along the amplified product. The preferred sequence for the probe sequence would contain the exon-exon junction or sequences complementary thereto.

The use of single or double stranded cDNA as starting material for the cyclic amplification differs only in the initial priming and extension reactions; with single stranded material, the synthesis of the first extension product is required before the second primer can anneal and initiate amplification. With double stranded cDNA, both primers can initiate the first cycle of amplification. In either instance, the product of the chain reaction is a discrete nucleic acid duplex with termini corresponding to the ends of the specific primers employed.

PREFERRED EMBODIMENT

The methods of the present invention for detection of chimeric mRNA are especially preferred for the detection of chimeric mRNA that is indicative of aberrant chromosome rearrangements. Such rearrangements give rise to alternate mRNA splicing that relate to neoplastic cell types and stages of neoplastic development.

Chromosome rearrangement such as translocations and inversions give rise to misalignment of different gene coding sequences and result in the production of chimeric mRNA that contain exons derived from unrelated genes. In certain instances, these chimeric mRNAs translate into proteins associated with certain types of cancers.

The methods of the invention can be used to detect the exon-exon junctions in chimeric mRNA junctions present in minute quantities. This is highly advantageous for determining an aberrant chimeric mRNA expressed by a particular neoplastic cell when the cell represents a very small percent of the total number of cells in a clinical sample. For example, the method can be used for early diagnosis of leukemia when the number of cancerous cells is small or for monitoring treated patients for the presence of reoccurring cancer cells.

The methods of the invention can be used to detect mRNA sequences from any type of biological or clinical sample, such as tissue biopsy taken from bone marrow, breast, liver, lung, lymph modes, brain or colon.

To amplify and detect a specific chimeric mRNA sequence, the sequences surrounding the exon-exon junctions between the two contributing exons must be known. To obtain this information, cloned cDNA and genomic sequences are compared by Southern analysis and sequencing. The genomic sequences that interrupt sequences common to both pinpoint the intron-exon junctions and the corresponding exon termini between the two exons of the chimeric mRNA. Using this approach, Shtivelman, supra, has determined the exon-exon junctions of the BCR-ABL gene contained on the Philadelphia chromosome.

For purposes of the present invention, the design of oligonucleotide primers both for initiation of cDNA synthesis and for PCR amplification is well within the skill of one of ordinary skill in the art. Briefly, to initiate cDNA synthesis, the choice of oligonucleotide primer depends on the size of the chimeric mRNA, whether the chimeric mRNA has a poly A tail, and how far away from the poly A tail the exon-exon junction is located.

If the chimeric mRNA contains a poly A tail and the region to be amplified is located near the poly A tail, the use of oligo d(T) as a primer for cDNA synthesis is generally suitable for purposes of the present invention. When an oligo d(T) primer is used to initiate cDNA synthesis, the primer pair for PCR amplification is determined by choosing two short stretches of sequence flanking the exon-exon junction and separated by between 100 to 300 base pairs, although separation by greater distances is within the scope of the present invention. The junction can be located at any point between the sequences, but is preferably centrally located. The first primer of the primer pair will anneal to the cDNA copy of the chimeric mRNA at sequences located on the 3' side of the junction contained in the cDNA. The primer will have a sequence that is substantially homologous to sequences of the chimeric mRNA that are located on the 5' side of the junction contained in the chimeric mRNA except for having thymine bases in place of uracil. The 3' hydroxyl of the first primer will initiate synthesis of a first DNA sequence across the junction contained in the cDNA. The second primer of the primer pair will anneal to sequences of the first DNA sequence that are 3' of the junction contained in the first DNA sequence. The second primer will have a sequence that is substantially complementary to sequences of the chimeric mRNA that are located on the 3' side of the junction contained in the chimeric mRNA, and will have thymine bases in place of uracil. The 3' hydroxyl of the second primer will initiate synthesis of a second DNA sequence across the junction contained in the first DNA for which it is complementary, forming a duplex DNA molecule that contains the junction. This new molecule will act as template to initiate further cycles of repeated primer annealing and extension-product synthesis, causing the amount of product, a discrete DNA duplex with termini corresponding to the ends of the specific primers employed, to exponentially increase.

When the region of the chimeric mRNA that contains the exon-exon junction is located far from the poly A tail or if the chimeric mRNA does not have a poly A tail, the use of a downstream primer for initiation of cDNA synthesis is preferred. It should be noted that, in general, the use of the downstream primer as the primer for initiation of cDNA synthesis is preferred because fewer different oligonucleotides are required.

Once amplified, the sequence can be detected through any means commonly known in the art of nucleic acid detection. For example, amplification, if it occurs, will give a sequence of known size that can easily be determined by agarose gel electrophoresis. In addition, the amplified sequence can be detected through hybridization with an oligonucleotide probe. The probe can be labeled by any means that is amenable to any detection method. For example, the probe can be labeled with radioisotopes such as $^{32}P$, $^{3}H$, $^{35}S$ or $^{125}I$ and detected by autoradiography or radiometry. In addition, the probe can be labeled with a peroxidatic enzyme such as horseradish peroxidase (HRP) and detection can be done using chromogenic substrates such as 3,3'5,5'-tetramethylbenzidine. Methods for preparing HRP-labeled oligonucleotides are disclosed in copending U.S. patent application Ser. Nos. 103,978 and 104,200, both filed Oct. 2, 1987, incorporated herein by reference.

Alternatively, detection of the amplified sequence can be achieved by using primers labeled at the 5' terminus with affinity molecules such as biotin and incorporating the label into product during the Polymerase Chain Reaction. The amplified product can then be hybridized to an immobilized sequence specific probe. If biotin is incorporated into the amplified sequence, the hybridized sequence can be detected by binding with a conjugate of streptavidin and horseradish peroxidase, and reacting the bound conjugate with a chromogenic substrate such as 3,3',5,5'-tetramethylbenzidine (TMB). Methods of making and using probes immobilized onto nylon are disclosed in U.S. application Ser. No. 197,000, filed May 20, 1988, incorporated herein by reference.

The probe can be designed to hybridize with any sequence along the amplified sequence. The probe sequence can be specific for sequences unique to either exon or more preferably, it can be specific for a "chimeric" sequence which contains sequences from both exons with the exon-exon junction between.

The Philadelphia chromosome ($Ph^1$) associated with chronic myeloid leukemia (CML) and acute lymphocytic leukemia (ALL) results from a reciprocal translocation t(9;22) that fuses the ABL oncogene on chromosome 9 to sequences within the BCR gene on chromosome 22. This translocation gives rise to the expression of a novel protein having increased tyrosine kinase activity. The scientific evidence suggests that the altered protein is involved in the development of CML and some cases of ALL. The breakpoints in chromosome 22 have been shown to occur within two or more introns of the BCR gene, Heisterkamp, N., et al. Nature 315: 758–761 (1985), incorporated herein by reference. The breakpoints in chromosome 9 are upstream from the ABL exon II. The resulting sequence on the Philadelphia chromosome bears the 5' portion of the BCR gene fused head to tail with most of the ABL gene. The regulatory sequence of the BCR gene controls expression of a chimeric mRNA sequence containing exons from both genes.

It is known that at least three distinct BCR-ABL mRNAs exist, two from variants of CML and one from ALL. These mRNAs contain one of three different BCR exons fused to the same ABL exon. The present invention provides primer pairs designed to selectively amplify each of the three unique junctions. For example, one primer specific for sequences in one of the 3 BCR exons can be paired with a primer complementary to sequences in the common ABL exon. The choice of BCR primer will determine which chimeric mRNA will be amplified. Detection is achieved using an oligonucleotide probe specific for the unique BCR-ABL junction. In this manner, the different CML and ALL variants are distinguished. In addition, the invention provides primer-pairs to amplify any combination of BCR-ABL exon fusions that define new and diagnostically important chimeric mRNAs associated with cancers such as CML and ALL.

An important aspect of the invention are kits that allow quick and convenient diagnosis of diseases associated with aberrant chimeric mRNA expression that results from genetic rearrangement. These kits contain primers and probes for amplifying and detecting sequences of cDNA complementary to a particular chimeric mRNA. For example, kits for diagnosing the CML and ALL variants contain primers to the 3 BCR exons and the 1 ABL exon and oligonucleotide probes to detect each of the 3 unique chimeric mRNAs. In addition, PCR reagents, i.e., buffer, deoxyribonucleoside 5'-triphosphates, and polymerase are included, as well as reagents for synthesizing cDNA, i.e., reverse transcriptase, buffer, oligo-(dT) primer if desired, and deoxyribonucleoside 5'-triphosphates.

The following examples are offered by way of illustration only and should not be construed as intending to limit the invention in any manner.

EXAMPLE 1

Detection of Chronic Myeloid Leukemia

This example demonstrates the detection of leukemia-specific chimeric mRNA for diagnosis of chronic myeloid leukemia by the methods of the invention.

A. Karyotype Analysis of Clinical Samples

Blood was drawn from patients after informed consent. White cells were fractionated on Ficoll TM (Pharmacia, Sweden) gradients and isolated as the light density fractions. Karyotype determination was done at the UCLA cytogenetics laboratory. Patient 1 was diagnosed as Philadelphia chromosome negative ($Ph^1$-) with myelo-proliferative syndrome (MPD). Patient 2 and Patient 3 were in an accelerated stage of CML, while Patient 4 was in the chronic stage. Patients 2, 3 and 4 contained both $Ph^1$ and 9q+ chromosomes, suggesting the presence of the usual t(9;22) reciprocal translocation.

B. Immuno-Type Analysis of Patient Samples

The samples were analyzed for the presence of the $P210^{bcr-abl}$ fusion protein and the normal $P145^{c-ABL}$ protein. The data is shown in FIG. 1. Panels A and C are from the K562 cells which synthesize both P210 and P145 proteins. Panel B, D, E are from Patients 1, 2 and 3, respectively. Protein analysis was impossible for Patient sample 4, because of the poor quality of the cells, illustrating further the disadvantage such analysis has for diagnostics. The data in panels A and B were obtained by immunoprecipitation of the samples labelled in vivo with $^{32}$P-orthophosphate by the method of Konopka, J. B., In. Virol. 51:223 (1984), incorporated herein by reference. The antisera used were: 1=normal rabbit, 2=rabbit anti-pEx5 and 3=rabbit anti-pEx2 sera (pEx2 and pEx5 correspond to fusion proteins, expressed in bacteria, that correspond to separate regions of the v-ABL protein, Konopka, supra). The data in panels C-E were obtained using the in vitro kinase assay described by Clark, S. S., et al. Science 235:85 (1987), incorporated herein by reference. The samples were analyzed by SDS-Page electrophoresis on 8% gels followed by autoradiography. Philadelphia chromosome diagnosis is indicated by + or −, where + indicates presence of the Philadelphia chromosome.

The results show Patients 2 and 3 (panels D and E) to have the characteristic 210 kilodalton BCR-ABL fusion protein (the P210 protein), while Patient 1 (panel B) shows only the normal P145 c-ABL protein. The K562 control cells (panels A and C) show the expected results of having both the P210 and P145 proteins.

C. RNA Extraction, cDNA Preparation, PCR and Analysis

RNA was isolated from cell lines as described by Kawasaki et al. Science 230:291 (1985), incorporated herein by reference. Total cellular RNA was isolated from clinical samples by homogenization in guanidinium isothiocyanate followed by direct precipitation of RNA from guanidinium by 4M LiCl, as described by Cathala, G., et al. DNA 2:329 (1983), incorporated herein by reference. One μg of total RNA was used as template for the amplification reactions, and one tenth of the total sample (5 μl from 50 μl) was used from the clinical RNA isolates. RNA from the clinical samples (~$10^7$ cells) was not quantitated, because analysis by gel electrophoresis indicated that the samples were heavily contaminated with nuclear DNA. K562 is a $Ph^1$ chromosome positive cell line (Lozzio, C. G. and Lorrio, B. B., Blood 45:321 (1975), incorporated herein by reference), and HL-60 is a Ph[1]-negative myeloid cell line (Collins, S. J., et al. Nature 270:347 (1977), incorporated herein by reference).

Complementary DNA (cDNA) was synthesized using MuLV reverse transcriptase (Bethesda Research Labs Inc., P.O. Box 6009, Gaithersburg, Md. 20877) essentially following the manufacturer's protocol. The 20 μl reaction contained 1X enzyme buffer (supplied by BRL), various RNA samples, 1 μl of RNAsin (Promega Biotec, 2800 South Fish Hatchery Road, Madison, Wis.), 1 mM of each deoxynucleoside triphosphate and 200 units of reverse transcriptase and 10 pmoles of downstream primer, which also served as the second primer in the amplification reaction. The sequence of the second primer, called CML II, is given below. The reaction was incubated for 30 min. at 37 C.

The reaction was then diluted with 80 μl of PCR buffer (50 mM KCl, 50 mM Tris-Cl, 2.5 mM $MgCl_2$, 100 μg/ml BSA, pH 8.4), and 40–50 pmoles of the first PCR primer, 50 pmoles of the second primer, and one unit of the thermostable DNA polymerase (Taq polymerase) were then added to the mixture. The sequence of the first primer, called CML I, is given below. Methods of producing and cloning Taq enzyme are disclosed in commonly owned and copending U.S. patent application Ser. Nos. 899,241, 063,509, and 143,441, incorporated herein by reference. Methods of amplifying DNA sequences using Taq are described in commonly owned and copending U.S. patent application Ser. Nos. 899,513 and 063,647, both incorporated herein by reference. About 150 μl of mineral oil were layered over the reaction mixture to prevent evaporation.

The reaction was started by heat denaturating the RNA-cDNA hybrid for 20 sec. at 95 C., annealing the primers for 15 sec. at 55 C., and then extending the primers for 1 min. at 72 C. Heat denaturation started the cycle over again and was repeated 40–50 times using a programmable heating block manufactured by Perkin-Elmer Cetus instruments and disclosed in commonly owned and copending U.S. patent application Ser. No. 899,061, incorporated herein by reference. After the final cycle, the temperature was held at 72 C. for 10 min. to allow reannealing of the amplified products and then chilled. Ten μl of each reaction were run on composite gels containing 3% NuSieve®/1% SeaKem® agarose (FMC BioProducts, 5 Maple Street, Rockland, Me.) in Tris-Borate-EDTA (TBE) buffer. Gels were stained with ethidium bromide, photographed and then blotted onto Zeta-Probe® membrane (Bio-Rad, 1414 Harbour Way South, Richmond, Calif. 94804) using the alkaline transfer protocol of Reed, K. C. and Mann, D. Nucleic Acid Res. 13: 7207 (1985) or onto nitrocellulose by the method of Southern, E. M., J. Mol. Biol. 98: 503 (1975), both incorporated herein by reference.

The membranes were prehybridized for 1 hr. at 60 C. in 5XSSC, 5X Denhardt's (5X Denhardt's is 1 g Ficoll®, 1 g polyvinylpyrrolidone, 1 g BSA in 100 ml $H_2O$), 20 mM sodium phosphate (pH 7.0), 5 mM EDTA, 200 μg/ml yeast RNA, and 1% Sarkosyl® (SIGMA Chemical Co., P.O. Box 14508, St. Louis, Mo. 63178). The buffer was removed and replaced with the same containing one million cpm/ml of $^{32}P$ 5'-end labelled oligonucleotides. Hybridization was for 5–6 hrs. at 60 C. Washing was done at 60 C in 5XSSC-0.1% SDS. Blots were autoradiographed using Kodak XAR® film at −70 C. The marker is the 123 base pair ladder from BRL.

Oligonucleotides were synthesized on a BioSearch SAM-1® DNA synthesizer. The oligonucleotides used for amplification primers and probes for CML are depicted below. DNA sequences used for the CML studies were reported by Heisterkamp, N., et al. Nature 315: 758 (1985); Grosveld, G., et al. Mol. Cell. Biol. 6: 607 (1986); and Shtivelman, E., et al. Cell 47: 277 (1986), all of which are incorporated herein by reference.

| CML Oligonucleotides | |
| --- | --- |
| CML I | 5' GGAGCTGCAGATGCTGACCAAC 3' |
| CML II | 5' TCAGACCCTGAGGCTCAAAGTC 3' |
| CML III | 5' GCTGAAGGGCTT ↑ TTGAACTCTGCTTA 3' |
| CML IV | 5' GCTGAAGGGCTT ↑ CTTCCTTATTGATG 3' |

CML I is the first PCR primer (complementary to cDNA sequences within the BCR exon 2) and CML II is the second PCR primer (homologous to cDNA sequences within the ABL exonII and is also the downstream primer that initiates cDNA synthesis). CML III is the probe for detecting BCR exon 3/ABL exon II chimeric mRNA in the present method, and CML IV is the probe for BCR exon 2/ABL exon II chimeric mRNAs. Enumeration of the BCR exon is from Heisterkamp, supra, and enumeration of the ABL exon is from Shtivelman, supra. The junction probes are complementary to the coding sequences of the respective chimeric mRNAs; the arrows ( ↑ ) denote the junction between BCR and ABL. When BCR exon 3 is present in the chimeric mRNA, a 200 base pair (bp) fragment is amplified; when BCR exon 2 is present, a 125 bp fragment is amplified.

Figure 2:
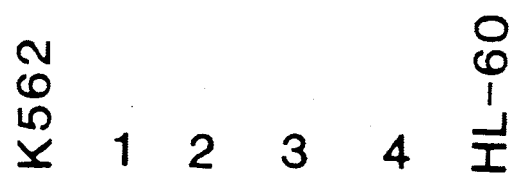
FIG. 2 depicts an autoradiograph of a Southern transfer of the PCR-amplified cDNA prepared from a chimeric mRNA sequence from each of the CML patient samples and shows the detection of the junction between BCR exon 3 and ABL exon II using the oligonucleotide primers CML-I and CML-II and the $^{32}P$ labeled oligonucleotide probe, CML-III.
Figure 2:

The Southern hybridization results using the CML III oligonucleotide probe are shown in FIG. 2. The amplified DNA from Patient 3 (lane 3) and the positive control, cell line K562, hybridized to the probe, indicating that the BCR-ABL junction in the chimeric mRNA present in the two samples are the same. The negative control, a Ph[1]-negative HL-60 sample, which contains normal, i.e., unfused, BCR and ABL chimeric mRNA, did not hybridize to the probe, because no amplification occured.

Figure 3:
FIG. 3 depicts an autoradiograph of the same Southern transfer shown in FIG. 2 that was stripped of the CML-III probe and rehybridized with a CML-IV probe and shows the detection of the splice junction between BCR exon 2 and ABL exon II.

The same blot was stripped of the CML III probe and rehybridized with the CML IV oligonucleotide probe, which is specific for chimeric mRNAs that contain a BCR exon 2/ABL exon II junction. The results of the hybridization are shown in FIG. 3. Both clinical samples 2 and 4 (lanes 2 and 4) show strong hybridization with the probe, demonstrating their BCR-ABL junctions to be the same, but different from Patient 3 and the K562 mRNA. The sample from Patient 1 (lane 1) hybridized to neither probe, consistent with the Ph[1]-negative cytogenetic diagnosis, the lack of $P210^{BCR-ABL}$ protein, and the fact that no amplification occured.

The results indicate that the present methods are not only accurate but also provide information previously unknown. Two of the patients (1 and 4) had Ph[1] translocation resulting in chimeric mRNA containing a BCR exon 2/ABL exon II fusion, while Patient 3 had chimeric mRNA containing a BCR exon 3/ABL exon II fusion. Normal diagnostic procedures cannot differentiate between these two types of translocations.

EXAMPLE 2

Detection of Acute Lymphocytic Leukemia

This example demonstrates the detection of chimeric mRNA sequences specific to acute lymphocytic leukemia (ALL) by the methods of the invention.

As described in example 1, RNA was isolated from SUP-B15, a cell line derived from a Ph[1] positive ALL patient. This cell line has been shown to express a P185$^{BCR-ABL}$ protein and a 7 kilobase BCR-ABL chimeric mRNA (Clark, et al. Science 239: 775–777 (1988), incorporated herein by reference).

Oligonucleotides were synthesized as described in Example 1. The oligonucleotides used for amplification primers and probes for ALL are given below. The ALL DNA sequences used to derive the oligonucleotide sequences are reported by Hermans, A., et al. Cell 51: 33 (1987), Fainstein, E. Nature 330: 386 (1987), and Clark, supra, incorporated herein by reference.

| ALL oligonucleotides | |
|---|---|
| ALL I | 5' CGCATGTTCCGGGACAAAAGC 3' |
| ALL II | 5' GGTCATTTTCACTGGGTCCAGC 3' |
| ALL III | 5' GCTGAAGGGCTT ↑ CTGCGTCTCCAT 3' |

ALL I is the first PCR primer (complementary to cDNA sequences within the most 5' BCR exon) and ALL II is the second PCR primer (homologous to cDNA sequences within the ABL exon II, and the downstream primer for initiation of cDNA synthesis). ALL III is the junction probe with the arrow denoting the junction between BCR and ABL. Amplification of the ALL sequence yields a 307 bp product.

cDNA preparation, PCR amplification and Southern hybridization were done in substantial accordance with the procedure described in example 1. Cell line K562 was used as a negative control. If present, the amplified mRNA from Patients 1–4 was also analyzed.

Figure 4:
FIG. 4 depicts an autoradiograph of a slot blot analysis to illustrate the sensitivity of the present methods.

The results, depicted in FIG. 4, show the amplification reaction from SUP-B15 total RNA to give a strong hybridization signal with the ALL III probe. In addition, the CML patients 2 and 3 (lanes 2 and 3) lacked discernable hybridization, demonstrating that Ph[1]-positive ALL BCR-ABL chimeric mRNA can be easily distinguished from CML BCR-ABL chimeric mRNA by the methods of the invention.

EXAMPLE 3

Sensitivity of Chimeric mRNA Detection

This example demonstrates that the methods of the invention are sensitive to the extent that less than one cell equivalent of total cytoplasmic RNA is required for detection.

Cell line K562 cytoplasmic RNA was diluted in 10-fold increments up to $10^7$-fold using 10 µg/ml yeast RNA as the diluent and carrier for the cDNA-PCR reaction. The diluted material was amplified by the cDNA-PCR method as described in Example I using primers CML I and CML II. One-tenth of the reaction mixture was slot-blotted onto nitrocellulose with a Schleicher & Schuell apparatus. The blot was hybridized with the CML III probe. A Ph[1] negative T-cell leukemia line, designated Jurkat, Hansen, J. A., et al. Immunogenetics 10: 247 (1980), incorporated herein by reference, was included as the negative control.

Figure 5:
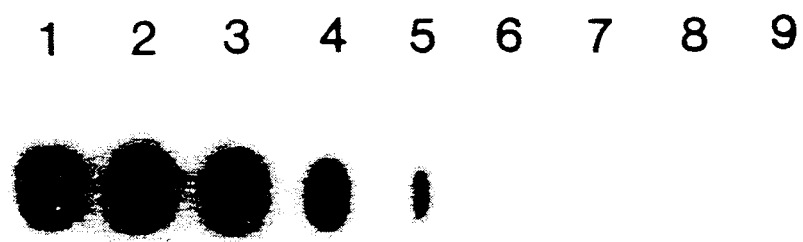
FIG. 5 depicts an autoradiograph of a Southern transfer of the PCR-amplified cDNA prepared from a chimeric mRNA sequences from an ALL Ph[1]+cell line, SUPB15, and samples from patients diagnosed with CML showing the detection of the junction between the 5′ BCR exon and ABL exon II using the oligonucleotide primers ALL-1 and ALL-II and the $^{32}P$ labeled oligonucleotide probe ALL III.

The results are shown in FIG. 5. Slots 1–7 contain the diluted K562 RNA after amplification. Slots 8 and 9 contain buffer and Jurkat mRNA negative controls, respectively. With the undiluted RNA sample in slot 1, the final dilution in slot 7 represents 1 pg of K562 RNA. A positive hybridization signal is easily detectable at the $10^5$-fold dilution in slot 6. There was 10 pg of K562 RNA at the $10^5$-fold dilution, but because only one-tenth of the reaction was actually analyzed, the signal is derived from the amplified product of 1 pg of total cytoplasmic RNA.

One µg of RNA is roughly equivalent to the amount contained in the cytoplasm of $10^5$ K562 cells (10 pg cytoplasmic RNA per cell). Thus, the $10^5$-fold dilution contains the RNA from about one K562 cell. Because just one-tenth of the reaction was used for analysis, the positive signal represents the amplified product of less than one cell equivalent. This results demonstrates that diagnosis is feasible even when the leukemic cells are present in extremely small numbers.

EXAMPLE 4

General Methods For Chimeric mRNA Amplification

A. Reverse Transcriptase Reaction

The reaction is done in 10–20 µl of 1X PCR buffer (50 mM KCl, 20–50 mM Tris-Cl, 2.5 mM MgCl$_2$, 100 µg/ml bovine serum albumin (BSA), pH 8.4), 1.0 mM of each deoxynucleoside triphosphate (dATP, dCTP, dTTP, dGTP), 0.1 µg oligo d(T) or 10–50 pmoles downstream primer, 1 unit/µl RNAsin, RNA sample and 100–200 units of MuLV reverse transcriptase. Because magnesium concentration is crucial for enzyme activity, care should be taken that addition of other reagents does not lower the magnesium molarity (i.e., some nucleic acid samples contain 1 mM EDTA which can chelate much of the magnesium). In general, the magnesium molarity should be at least 2 mM. The reaction is incubated for 30 minutes at 37 C.–42 C., and then stopped by placing it in a 95 C. water bath for 3–5 minutes to heat kill the reverse transcriptase. This also gives a better defined amplification product.

B. Polymerase Chain Reaction

Four volumes of 1X PCR buffer is added to the heat inactivated reverse transcriptase reaction plus 0–50 pmoles downstream primer (amount depends on the amount used in the reverse transcriptase reaction), 10–50 pmoles upstream primer and 1–2 units of Taq polymerase. The reaction mixture is overlayed with approximately 200 µl of mineral oil to prevent evaporation.

The Polymerase Chain Reaction cycles are initiated by first heating the denatured reverse transcriptase reaction at 95 C. for 20–30 seconds. The reaction temperature is then lowered to 55 C. for 15–30 seconds to allow the primers to anneal. Next, the primers are extended by raising the reaction temperature to 72 C. The degree of extension is related to the length of time at 72 C. For example, under optimal conditions, the amplification of a 1 kb fragment is best achieved with a 1 minute extension time. However, reaction conditions will vary, and it may be necessary to try different extension times for best results. Once the extension time is over, the PCR cycles are started again by raising the reaction temperature to 95 C. The time specified for denaturation, annealing and extension is the actual time the solutions are at the specified temperature.

The number of cycles will vary depending on the amount of starting material and the degree of amplification desired, but readily can be determined empirically.

It is best to use the lowest number of PCR cycles that give the cleanest results. Too many cycles may give extraneous extension products. In addition, with high numbers of PCR cycles, sample contamination begins to appear, i.e., false positives will develop due to the presence of extremely low levels of contamination.

If amplification does not occur when expected, one of two approaches can be taken. The first involves trying a new set of oligonucleotide primers that are upstream or downstream from the original set. It is possible that mRNA secondary structure is interfering with hybridization of one or both of the primers, thus preventing extension by the reverse transcriptase reaction. The second involves using oligo d(T) as the primer in the reverse transcriptase reaction. Try using 10–20 pmoles of oligo $d(T)_{12-18}$ or between 0.05 and 0.1 µg of oligo d(T).

It is also helpful to titrate the PCR primers to find the lowest amount that can be used to give a well defined amplified product. Too large an excess of primers causes the amplification of extraneous products that hinders subsequent analysis. As low as 5 pmoles of primers have been used to give efficient amplification.

The invention has been described in detail with particular reference to preferred embodiments thereof, but it will be understood that variations and modifications can be effected within the spirit and scope of the following claims.

What is claimed is:

1. A method for detecting a chimeric mRNA in a biological sample, wherein said chimeric mRNA is associated with acute lymphocytic leukemia (ALL) and comprises a BCR exon in junction with an ABL exon, the method has the step of:
   a) synthesizing cDNA from mRNA in said sample;
   b) contacting said cDNA with a first and second primer, wherein said first primer is homologous to a sequence contained in said BCR exon and said second primer is complementary to a sequence in said ABL exon to provide a mixture for amplifying chimeric mRNA associated with ALL;
   c) treating the mixture prepared in step (b) under conditions and with reagents suitable for amplifying said cDNA segment by a polymerase chain reaction; and
   d) determining if amplification has occurred.

2. The method of claim 1 wherein said determining step comprises contacting the mixture prepared in step (c) with an oligonucleotide probe under hybridizing conditions and determining whether hybridization has occurred, wherein said probe is selected from the group consisting of a probe having a sequence that is homologous to said chimeric mRNA sequence contained in said cDNA and a probe having a sequence that is complementary to said chimeric mRNA sequence contained in said cDNA.

3. The method of claim 2, wherein said probe for detecting chimeric mRNA associated with acute lymphocytic leukemia consists essentially of the sequence: 5'-GCTGAAGGGTTCTGCGTCTCCAT-3'.

4. The method of claim 1 wherein said first primer has the sequence:

5'CGCATGTTCCGGGACAAAAGC3', and said second primer has the sequence:

5'GGTCATTTTCACTGGGTCCAGC3'.

5. A method for detecting a chimeric mRNA in a biological sample, wherein said chimeric mRNA is associated with chronic myeloid leukemia (CML) and comprises a BCR exon in junction with an ABL exon, the method has the steps of:
   a) synthesizing cDNA from mRNA in said sample;
   b) contacting said cDNA with a first and second primer, wherein said first primer has the sequence:

5'GGAGCTGCAGATGCTGACCAAC3', and said second primer has the sequence:

5'TCAGACCCTGAGGCTCAAAGTC3', to provide a mixture for amplifying chimeric mRNA associated with CML;
   c) treating the mixture prepared in step (b) under conditions and with reagents suitable for amplifying said cDNA segment by a polymerase chain reaction; and
   d) determining if amplification has occurred.

6. The method of claim 5, wherein said determining step comprises contacting the mixture prepared in step (c) with an oligonucleotide probe, and said oligonucleotide probe has the sequence:

5'GCTGAAGGGCTTCTTCCTTATTGATG3'.

7. The method of claim 5 wherein said determining step comprises contacting the mixture prepared in step (c) with an oligonucleotide probe, and said oligonucleotide probe has the sequence:

5'GCTGAAGGGCTTTTGAACTCTGCTTA3'.

8. A method for distinguishing between chimeric mRNA associated with chronic myeloid leukemia (CML) and chimeric mRNA associated with acute lymphocytic leukemia (ALL), in a biological sample, wherein said chimeric mRNAs each comprise a BCR exon in junction with an ABL exon, the method has the steps of:
   a) synthesizing cDNA from mRNA in said sample;
   b) contacting said cDNA with a first and second primer for amplifying chimeric mRNA associated with CML that contains an exon-junction between a BCR exon and an ABL exon;
   c) treating the mixture prepared in step (b) under conditions and with reagents suitable for amplifying said cDNA segment by a polymerase chain reaction; and
   d) contacting said cDNA of step (a) with a third and fourth primer, for amplifying chimeric mRNA associated with ALL that contains an exon-junction between a BCR exon and an ABL exon;
   e) treating the mixture prepared in step (d) under conditions and with reagents suitable for amplifying said cDNA segment by a polymerase chain reaction; and
   f) determining if amplification has occurred in each of step (c) and step (e).

9. The method claim 8, wherein said determining step (f) comprises:
   (1) contacting the mixture prepared in step (c) with an oligonucleotide probe specific for an exon-junction between a BCR exon and an ABL exon contained within chimeric mRNA associated with chronic myeloid leukemia; and (2) contacting the mixture prepared in step (e) with an oligonucleotide probe specific for an exon-junction between a BCR exon and an ABL exon contained within chimeric mRNA associated with acute lymphocytic leukemia.

10. The method of claim 8, wherein said first primer has the sequence:

5'GGAGCTGCAGATGCTGACCAAC3';

said second primer has the sequence:

5'TCAGACCCTGAGGCTCAAAGTC3';

said third primer has the sequence:

5'CGCATGTTCCGGGACAAAAGC3';

and said fourth primer has the sequence:

5'GGTCATTTTCACTGGGTCCAGC3'.

11. The method of claim 9, wherein at step (f) (1) said probe comprises a sequence selected from the group of nucleic acid sequences consisting of:

5'GCTGAAGGGCTTTTGAACTCTGCTTA3';

and

5'GCTGAAGGGCTTCTTCCTTATTGATG3'.

12. The method of claim 9, wherein at step (f) (2) said probe comprises the sequence:

5'GCTGAAGGGCTTCTGCGTCTCCAT3'.

13. A kit for detecting a chimeric mRNA associated with chronic myeloid leukemia (CML), wherein said chimeric mRNA comprises a BCR exon in junction with an ABL exon, said kit comprising:
a) a first and second primer wherein said first primer has the sequence:
5'GGAGCTGCAGATGCTGACCAAC3', and said second primer has the sequence:

5'TCAGACCCTGAGGCTCAAAGTC3', b) an oligonucleotide probe.

14. The kit of claim 13 wherein said oligonucleotide probe has the sequence:

5'GCTGAAGGGCTTCTTCCTTATTGATG3'.

15. The kit of claim 13 wherein said oligonucleotide probe has the sequence:

5'GCTGAAGGGCTTTTGAACTCTGCTTA3'.

16. A kit for detecting a chimeric mRNA associated with acute lymphocytic leukemia, wherein said chimeric mRNA comprises a BCR exon in junction with an ABL exon, said kit comprising:
a) a first and second primer where said first primer is homologous to a sequence contained in said BCR exon and said second primer is complementary to a sequence in said ABL exon; and b) an oligonucleotide probe specific for the exon junction between said BCR exon and said ABL exon.

17. The kit of claim 16 wherein said first primer has the sequence:

5'CGCATGTTCCGGGACAAAAGC3', said second primer has the sequence:

5'GGTCATTTTCACTGGGTCCAGC3', and said oligonucleotide probe has the sequence:

5'GCTGAAGGGCTTCTGCGTCTCCAT3'.

18. The kit of claim 16 that further comprises reagents for polymerase chain reaction.

19. A kit for distinguishing between chimeric mRNA associated with chronic myeloid leukemia (CML) and chimeric mRNA associated with acute lymphocytic leukemia (ALL), in a biological sample, wherein said chimeric mRNAs each comprise a BCR exon in junction with an ABL exon, said kit comprising:
a) a first and second primer for amplifying chimeric mRNA associated with CML which contains an exon-junction between a BCR exon and an ABL exon;
b) a third and fourth primer for amplifying chimeric mRNA associated with ALL which contains an exon-junction between a BCR exon and an ABL exon;
c) a first oligonucleotide probe specific for said chimeric mRNA associated with CML; and
d) a second oligonucleotide probe specific for said chimeric mRNA associated with ALL.

20. The kit of claim 19, wherein said first primer is

5'GGAGCTGCAGATGCTGACCAAC3';

said second primer is

5'TCAGACCCTGAGGCTCAAAGTC3';

said third primer is

5'CGCATGTTCCGGGACAAAAGC3';

and said fourth primer is

5'GGTCATTTTCACTGGGTCCAGC3'.

21. The kit of claim 19 that further comprises reagents for carrying out polymerase chain reaction.

22. The kit of claim 19, wherein said first probe has the sequence:

5'GCTGAAGGGCTTTTGAACTCTGCTTA3';

and said second probe has the sequence:

5'GCTGAAGGGCTTCTGCGTCTCCAT3'.

23. The kit of claim 19 that further comprises a third oligonucleotide probe, wherein said third probe is distinct from said first oligonucleotide probe and is specific for said chimeric mRNA associated with chronic myeloid leukemia.

24. The kit of claim 23 wherein said third probe has the sequence:

5'GCTGAAGGGCTTCTTCCTTATTGATG3'.

* * * * *

UNITED STATES PATENT AND TRADEMARK OFFICE
CERTIFICATE OF CORRECTION

PATENT NO. : 5,057,410

DATED : October 15, 1991

INVENTOR(S) : E. Kawasaki, F. McCormick, and O. Witte

It is certified that error appears in the above-identified patent and that said Letters Patent is hereby corrected as shown below:

On the cover page under the section entitled "Inventors:", line 3, delete "O. Witto" and insert therefor --N. Witte--.

Signed and Sealed this

Twenty-third Day of March, 1993

Attest:

STEPHEN G. KUNIN

*Attesting Officer*  *Acting Commissioner of Patents and Trademarks*